US010501506B2

(12) United States Patent
Nishi et al.

(10) Patent No.: US 10,501,506 B2
(45) Date of Patent: Dec. 10, 2019

(54) POLYPEPTIDE, AND USE THEREOF

(71) Applicants: KANEKA CORPORATION, Osaka-shi, Osaka (JP); NATIONAL INSTITUTE OF ADVANCED INDUSTRIAL SCIENCE AND TECHNOLOGY, Tokyo (JP)

(72) Inventors: Teruyuki Nishi, Takasago (JP); Kiyoshi Asai, Tokyo (JP); Hiroko Hagiwara, Tsukuba (JP); Masayuki Machida, Sapporo (JP)

(73) Assignees: KANEKA CORPORATION, Osaka-shi (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 33 days.

(21) Appl. No.: 14/901,005

(22) PCT Filed: Jun. 25, 2014

(86) PCT No.: PCT/JP2014/066807
§ 371 (c)(1),
(2) Date: Dec. 22, 2015

(87) PCT Pub. No.: WO2014/208584
PCT Pub. Date: Dec. 31, 2014

(65) Prior Publication Data
US 2016/0152669 A1 Jun. 2, 2016

(30) Foreign Application Priority Data

Jun. 26, 2013 (JP) ................. 2013-134037

(51) Int. Cl.
*C07K 14/39* (2006.01)
*C12P 21/02* (2006.01)
*C12N 15/81* (2006.01)

(52) U.S. Cl.
CPC .......... *C07K 14/39* (2013.01); *C12N 15/815* (2013.01); *C12P 21/02* (2013.01)

(58) Field of Classification Search
None
See application file for complete search history.

(56) References Cited

U.S. PATENT DOCUMENTS

2014/0058056 A1 2/2014 Burgard et al.

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
U.S. Office Action issued in U.S. Appl. No. 14/901,018 dated Sep. 14, 2016.
Curtin et al, "Dekkera bruxellensis AWRI1499_contig1660_scaffold21, whole genome shotgun sequence", Features, Origin, Database Genbank [online], Accession No. AHIQ01000135, (Region: 159305..160555), URL: http://www.ncbi.nlm.nih.gov/nuccore/385303550, Apr. 27, 2012 uploaded, retrieved on Sep. 3, 2014, 2 pages.
Curtin et al., "putative fungal zinc cluster transcription factor [Dekkera bruxellensis AWRI1499]", Features, Origin, Database Genbank [online], Accession No. EIF47683, URL: http://www.ncbi.nlm.nih.gov/protein/eif47683, Apr. 27, 2014 uploaded, retrieved on Sep. 5, 2014, 2 pages.
Dälken et al., "Maltose-Binding Protein Enhances Secretion of Recombinant Human Granzyme B Accompanied by In Vivo Processing of a Precursor MBP Fusion Protein", vol. 5, Issue 12 e14404, pp. 1-10, Dec. 2010.
De Schutter et al., "Pichia pastoris GS115 transcriptional regulatory protein (PAS_ccds)", Database Refseq [online], Accession No. XM_002490485, URL: http://www.ncbi.nlm.nih.gov/nuccore/254566838. Jul. 22, 2009 uploaded, retrieved on Sep. 3, 2014, 3 pages.
Gellissen, "Heterologous protein production in methylotrophic yeasts", Appl Microbiol Biotechnol 54, pp. 741-750, (2000).
International Search Report issued in PCT/JP2014/066807 dated Sep. 16, 2014.
Ning et al., "Expression, Purification, and Characterization of Humanized Anti-HBs Fab Fragment", J. Biochem, vol. 134, No. 6, pp. 813-817, 2003.
Ravin et al., "Ogataea parapolymorpha DL-1 chr5, whole genome shotgun sequence" Features, Origin, Database Genbank [online], Accession No. AEOI020000 (Region:1091493..1093445), URL: http://www.ncbi.nlm.nih.gov/nuccore/AEOI02000008.1, Dec. 3, 2013 uploaded, retrieved on Dec. 3, 2014, 3 pages.
Ravin et al., "Ogataea parapolymorpha DL-1 chr6, whole genome shotgun sequence", Features, Origin, Database Genbank [online], Accession No. AEOI02000009 (Region:complement (33055..33708)), URL: http://www.ncbi.nlm.nih.gov/nuccore/AEOI02000009.1, Dec. 3, 2013 uploaded, retrieved on Sep. 3, 2014, 2 pages.
Written Opinion of the International Searching Authority issued in PCT/JP2014/066807 dated Sep. 16, 2014.

(Continued)

*Primary Examiner* — Robert A Zeman
(74) *Attorney, Agent, or Firm* — Birch, Stewart, Kolasch & Birch, LLP

(57) ABSTRACT

This invention provides a novel means that allows efficient secretion and production of a target protein in a host cell. This invention concerns a novel polypeptide having an activity of improving the secretion productivity of a target protein, a gene comprising a nucleotide sequence encoding such polypeptide, a vector comprising such gene, a transformant obtained by transforming a host cell with such vector, and a method for producing a protein comprising a step of culturing such transformant and recovering a target protein from the culture product.

12 Claims, 1 Drawing Sheet
Specification includes a Sequence Listing.

(56) References Cited

OTHER PUBLICATIONS

EMBL Database Jan. 12, 2001 "T7 end of clone XBB0AA001C07 of library XBB0AA from strain CBS 4732 of Pichia angusta", XP002763620.
European Search Report issued in European Patent Application No. 14817026.9 dated Dec. 5, 2016.
European Search Report issued in European Patent Application No. 14818520.0 dated Nov. 14, 2016.
Gasser et al., "Engineering of Pichia Pastoris for Improved Production of Antibody Fragments", Biotechnology and Bioengineering, vol. 94, No. 2 (2006) pp. 353-361.
UniPort Database Jul. 7, 2009 "SubName: Full-Transcriptional regulatory proten {ECO:0000313:EMBL:CAY68429.1}"; XP002764410.
UniProt Database Mar. 19, 2014 "SubName: Full=Putative transcriptional regulatory proten {ECO:0000313:EMBL:ESW98779.1}"; XP002764409.

* cited by examiner

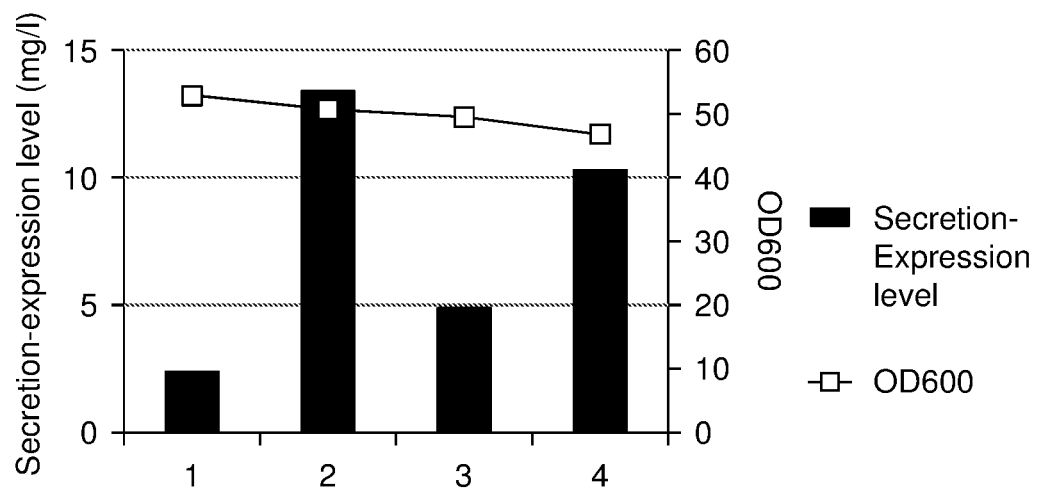

POLYPEPTIDE, AND USE THEREOF

TECHNICAL FIELD

The present invention relates to a novel polypeptide having an activity of improving the secretion productivity of a target protein in yeasts or other host cells, a gene encoding such polypeptide, and applications thereof.

BACKGROUND ART

In recent years, hosts for production of proteins of interest, such as animal cells (e.g., CHO), insects (e.g., silk worm), insect cells, animals (e.g., chickens and cows), and microorganisms (e.g., *E. coli* and yeast), have been used in order to produce proteins via genetic recombination. In particular, yeast cells can be cultured in large-scale, high-density culture systems in cost-effective media, and proteins can be produced at low cost. In addition, proteins can be secreted and expressed in a culture solution by using a signal peptide or the like, and a process for purifying proteins thus becomes easy. Further, yeast cells are advantageous in that they are eukaryotic organisms and post-translational modification such as glycosylation is possible. Accordingly, various studies have been made on yeast cells.

For example, Non-Patent Document 1 discloses a method for producing the green fluorescent protein, human serum albumin, the hepatitis B surface antigen, the human epidermal growth factor, and hirudin with the use of methanol-assimilating yeasts.

Non-Patent Document 2 discloses a method of introducing a gene comprising a nucleotide sequence encoding a partial antibody ligated to a site downstream of the alcohol oxidase (AOX) promoter into a yeast cell, thereby producing a low-molecular-weight antibody.

In addition, Non-Patent Document 3 discloses that productivity of a target protein is improved by introducing a gene comprising a nucleotide sequence encoding a solubility tag (e.g., glutathione-S-transferase (GST) or maltose-binding protein (MBP)) ligated to a nucleotide sequence encoding a target protein into a yeast cell.

When a yeast is used as a host that produces a protein via gene recombination, various attempts have been made in order to improve the productivity. Examples of such attempts include the addition of a signal sequence or tag to a gene encoding a target protein, the use of a potent promoter, codon modification, chaperon gene co-expression, and examination of host culture conditions.

PRIOR ART DOCUMENTS

Non-Patent Documents

Non-Patent Document 1: Appl. Microbiol. Biotechnol., December 2000; 54 (6): 741-50
Non-Patent Document 2: J. Biochem., December 2003; 134 (6): 813-7
Non-Patent Document 3: PLos ONE, 2010, vol. 5, e1 4404

SUMMARY OF THE INVENTION

Problem to be Solved by the Invention

The present invention provides a novel means that allows efficient secretion and production of a target protein in a host.

Means for Solving the Problem

The present inventors had attempted extensive analysis of the nucleotide sequence of chromosome DNA of *Ogataea angusta* in order to attain the above object. As a result, they discovered a gene encoding a novel polypeptide having an activity of improving the secretion productivity of a target protein. In addition, they had attempted to achieve high-level expression of the gene encoding the novel polypeptide in combination with a gene of a target protein in a yeast cell. As a result, they confirmed that the secretion productivity of a target protein would be improved, thereby completing the present invention.

Specifically, the present invention includes the following.
(1) A polypeptide (a), (b), or (c) below:
  (a) a polypeptide consisting of the amino acid sequence as shown in SEQ ID NO: 32 or 33;
  (b) a polypeptide consisting of an amino acid sequence derived from the amino acid sequence as shown in SEQ ID NO: 32 or 33 by substitution, deletion, insertion, and/or addition of one or a plurality of amino acids; or
  (c) a polypeptide consisting of an amino acid sequence having 85% or higher sequence identity with the amino acid sequence as shown in SEQ ID NO: 32 or 33.
(2) A gene (d), (e), (f), or (g) below:
  (d) a gene consisting of the nucleotide sequence as shown in SEQ ID NO: 9 or 34;
  (e) a gene consisting of a nucleotide sequence hybridizing under stringent conditions to a nucleotide sequence complementary to the nucleotide sequence as shown in SEQ ID NO: 9 or 34;
  (f) a gene consisting of a nucleotide sequence having 85% or higher sequence identity with the nucleotide sequence as shown in SEQ ID NO: 9 or 34; or
  (g) a gene consisting of a nucleotide sequence encoding a polypeptide consisting of the amino acid sequence as shown in SEQ ID NO: 32 or 33.
(3) A vector comprising the gene according to (2).
(4) A transformant obtained by transforming a host cell with the vector according to (3).
(5) The transformant according to (4), wherein the host cell is a yeast cell, bacteria cell, fungal cell, insect cell, or animal cell.
(6) The transformant according to (5), wherein the yeast is a methanol-assimilating yeast.
(7) The transformant according to (6), wherein the methanol-assimilating yeast belongs to the genus *Ogataea* or *Komagataella*.
(8) A method for producing a protein comprising a step of culturing the transformant according to any of (4) to (7) and recovering a target protein from the culture product.
(9) The method for producing a protein according to (8), wherein the culture is carried out with the use of glucose, and/or glycerol, and/or methanol as a carbon source.

This patent application claims priority from Japanese Patent Application No. 2013-134037 filed on Jun. 26, 2013, and includes part or all of the contents as disclosed in the description thereof.

Effects of the Invention

The present invention provides a novel polypeptide associated with an improvement in the secretion productivity of a target protein in a host and a gene encoding such polypeptide. High-level expression of the novel polypeptide according to the present invention in combination with a target protein in a host cell enables efficient secretion and production of such target protein.

BRIEF DESCRIPTION OF THE DRAWINGS

FIG. 1 shows the secretion-expression levels of a fully humanized anti-TNF-α Fab antibody by transformants prepared in the examples and the cell density (OD600) (1: a transformant of *Ogataea angusta* expressing a fully humanized anti-TNF-α Fab antibody, BMGY medium; 2: a transformant of *Ogataea angusta* expressing a novel polypeptide (pUCPgapNP1TmG418-introduced) and a fully humanized anti-TNF-α Fab antibody, BMGY medium; 3: a transformant of *Ogataea angusta* expressing a fully humanized anti-TNF-α Fab antibody, BMGMY medium; and 4: a transformant of *Ogataea angusta* expressing a novel polypeptide (pUCPgapNP1TmG418-introduced) and a fully humanized anti-TNF-α Fab antibody, BMGMY medium).

EMBODIMENTS FOR CARRYING OUT THE INVENTION

Hereafter, the present invention is described in detail with reference to preferable embodiments.
1. Polypeptide The polypeptide of the present invention is a novel polypeptide having an activity of improving the secretion productivity of a target protein in a host, and it consists of the amino acid sequence as shown in SEQ ID NO: 32 or 33.

The term "polypeptide" used in the present invention is composed of two or more amino acids joined by peptide bonds, including short-chain polypeptides generally referred to as peptides or oligopeptides.

In the present invention, the term "activity of improving the secretion productivity of a target protein" refers to an activity of increasing the amount of the target protein secreted and produced in the host cell and/or outside the host cell.

The polypeptide consisting of the amino acid sequence as shown in SEQ ID NO: 32 has a DNA-binding region. When high-level expression of such polypeptide is achieved in a host cell, the secretion productivity of a target protein is improved. The polypeptide consisting of the amino acid sequence as shown in SEQ ID NO: 33 is a sequence portion corresponding to amino acids residues from 114 to 149 in the amino acid sequence as shown in SEQ ID NO: 32, which is expected to be capable of binding to DNA. Thus, the polypeptide consisting of the sequence as shown in SEQ ID NO: 33 may be operably linked to another polypeptide, and high-level expression of the polypeptide may be achieved in a host cell. Thus, the secretion productivity of a target protein can be improved.

In the present invention, the term "expression" refers to transcription or translation of a nucleotide sequence that causes production of a polypeptide, which is a gene product. Such expression may be substantially constant regardless of conditions such as external stimulus or growth conditions, or it may be influenced by such conditions. A promoter that activates expression is not particularly limited, provided that such promoter activates expression of a nucleotide sequence encoding a target polypeptide.

The term "high-level expression" used in the present invention refers to an increased polypeptide level in a host cell or an increased mRNA level in the host cell, compared with a general level. For example, the polypeptide or mRNA level may be measured using an antibody that recognizes a polypeptide or by a technique such as RT-PCR, Northern hybridization, or hybridization using DNA arrays, and the determined level may be compared with that of a non-modified strain, such as a parent strain or wild-type strain. Thus, an increased polypeptide or mRNA level can be confirmed.

The high-level expression of the polypeptide can be realized by conventional techniques such as the induction of expression of a gene encoding the polypeptide of the chromosome and/or the vector (hereafter referred to as the "polypeptide gene"). In addition, such high-level expression of the polypeptide can be also realized by modification of the polypeptide gene of the chromosome and/or the vector (e.g., increase of the copy number, insertion of a promoter, or modification of a codon), introduction of the polypeptide gene into a host cell, or production of a strain expressing the polypeptide gene at high levels via introduction of a mutation into the host cell.

The polypeptide gene on the chromosome can be modified by introducing a gene into a host chromosome via homologous recombination, site-directed mutagenesis, or other techniques. For example, the polypeptide gene can be introduced into the chromosome so as to increase the number of copies, a promoter located upstream of the polypeptide may be substituted with a more potent promoter, or a codon can be modified to become more suitable as a host cell of the polypeptide gene.

A strain expressing the polypeptide gene at high levels via introduction of a mutation into the host cell can be obtained via conventional techniques, such as mutation of the host cell with the aid of a drug or ultraviolet rays, followed by selection of a strain expressing the polypeptide gene at high levels.

In addition to the polypeptide consisting of the amino acid sequence as shown in SEQ ID NO: 32, a polypeptide consisting of an amino acid sequence derived from the amino acid sequence as shown in SEQ ID NO: 32 by substitution, deletion, insertion, and/or addition of one or a plurality of amino acids is within the scope of the polypeptide of the present invention. The number of amino acids defined by the term "a plurality of amino acids" is not particularly limited, provided that an activity of the polypeptide consisting of the amino acid sequence as shown in SEQ ID NO: 32 for improving the secretion productivity of a target protein is retained. The number of amino acids is preferably up to 33, more preferably up to 30, further preferably up to 20, and most preferably up to 10, 5, 4, 3, or 2.

In addition to the polypeptide consisting of the amino acid sequence as shown in SEQ ID NO: 33, a polypeptide consisting of an amino acid sequence derived from the amino acid sequence as shown in SEQ ID NO: 33 by substitution, deletion, insertion, and/or addition of one or a plurality of amino acids is within the scope of the polypeptide of the present invention. The number of amino acids defined by the term "a plurality of amino acids" is not particularly limited, provided that an activity of the polypeptide consisting of the amino acid sequence as shown in SEQ ID NO: 33 for improving the secretion productivity of a target protein is retained. The number of amino acids is preferably up to 5, more preferably up to 4, further preferably up to 3, and most preferably up to 2.

In addition to the polypeptide consisting of the amino acid sequence as shown in SEQ ID NO: 32 or 33, a polypeptide consisting of an amino acid sequence having 85% or higher, preferably 90% or higher, more preferably 95% or higher, further preferably 97% or higher, and most preferably 99% or higher sequence identity with the amino acid sequence as shown in SEQ ID NO: 32 or 33 is within the scope of the polypeptide of the present invention.

A polypeptide consisting of an amino acid sequence having 85% or higher sequence identity with the amino acid sequence as shown in SEQ ID NO: 32 and having 85% or higher, preferably 90% or higher, more preferably 95% or higher, further preferably 97% or higher, and most preferably 99% or higher sequence identity with a portion of the amino acid sequence as shown in SEQ ID NO: 33 (amino acids residues from 114 to 149) is within the scope of the polypeptide of the present invention.

Amino acid sequence identity can be determined by a method well known in the art using sequence analysis software or the like. Examples thereof include the BLASTP programs using the BLAST algorithm and the FASTA programs using the FASTA algorithm. The amino acid sequence identity is determined by comparing the target amino acid sequence with the amino acid sequence as shown in SEQ ID NO: 32 or 33 and indicating a frequency of the same amino acids appearing at the same sites in percent figures.

2. Gene

The constitution and the functions of the gene of the present invention were first elucidated as a result of extensive analysis of the nucleotide sequence of chromosome DNA of *Ogataea angusta*. The gene of the present invention consists of the nucleotide sequence as shown in SEQ ID NO: 9 or 34. The "nucleotide sequence as shown in SEQ ID NO: 9 or 34" encodes a polypeptide consisting of the amino acid sequence as shown in SEQ ID NO: 32 or 33 described in 1. above.

In the present invention, the term "gene" refers to genetic information of an organism defined by a nucleotide sequence of DNA or RNA. It generally consists of a nucleotide sequence encoding a polypeptide. Such gene can be identified on the basis of the chromosome sequence with the use of gene search programs, annotation programs, or the like.

The gene of the present invention may consist of a nucleotide sequence hybridizing under stringent conditions to a nucleotide sequence complementary to the nucleotide sequence as shown in SEQ ID NO: 9 or 34. The "nucleotide sequence hybridizing under stringent conditions" can be, for example, a nucleotide sequence of DNA obtained by conducting hybridization in the presence of 0.7 to 1.0 M NaCl at 65° C. using a filter on which colony- or plaque-derived DNA is immobilized and washing the filter with a 2×SSC solution (a 1×SSC solution comprises 150 mM sodium chloride and 15 mM sodium citrate) at 65° C. Such nucleotide sequence of DNA can be obtained by washing the filter preferably with a 0.5×SSC solution at 65° C., more preferably with a 0.2×SSC solution at 65° C., and further preferably with a 0.1×SSC solution at 65° C.

Further, a gene consisting of a nucleotide sequence having 85% or higher, preferably 90% or higher, more preferably 95% or higher, further preferably 97% or higher, and most preferably 99% or higher sequence identity with the nucleotide sequence as shown in SEQ ID NO: 9 or 34 is within the scope of the gene of the present invention.

Nucleotide sequence identity can be determined by a method well known in the art using sequence analysis software or the like. Examples thereof include the BLASTN programs using the BLAST algorithm and the FASTA programs using the FASTA algorithm. The nucleotide sequence identity is determined by comparing the target nucleotide sequence with the nucleotide sequence as shown in SEQ ID NO: 9 or 34 and indicating a frequency of the same nucleotides appearing at the same sites in percent figures.

The "nucleotide sequence as shown in SEQ ID NO: 9 or 34" may not be derived from *Ogataea angusta*. Such nucleotide sequence may be prepared via PCR or other techniques from other mammalian animals, insects, fungi, bacteria, or phage display libraries. Alternatively, the target nucleotide sequence may be fully synthesized based on such nucleotide sequence. For example, a DNA primer designed based on the nucleotide sequence as shown in SEQ ID NO: 9 or 34 is synthesized, chromosome DNA is isolated from a yeast and the like, and PCR is carried out using the chromosome DNA as a template and the above DNA primer. Thus, the target nucleotide sequence can be obtained.

3. Vector

The vector of the present invention comprises the gene described in 2. above, and it is introduced into a host cell, so as to achieve high-level expression of the polypeptide described in 1. above.

The term "vector" used in the present invention refers to a nucleic acid molecule having a function of expressing a target gene in a transformed host cell. The vector has, for example, an expression cassette, a homologous recombination region, a selection marker gene, such as an auxotrophic marker gene or drug resistance gene, and an autonomously replicating sequence. After transformation, the vector may be integrated into the chromosome, or it may be present in the form of an autonomously replicating vector. Examples of autonomously replicating vectors include the YEp vector, the YRp vector, and the YCp vector. In the case of *Ogataea* yeasts, examples of vectors include, but are not particularly limited to, the pPICHOLI, pHIP, pHRP, and pHARS vectors.

The "expression cassette" is composed of the polypeptide gene and a promoter to express such polypeptide gene. The expression cassette may comprise a terminator. The expression cassette can be constructed in a plasmid such as pUC19, or it can be prepared via PCR.

The term "promoter" refers to a nucleotide sequence region located upstream of a polypeptide gene. In addition to RNA polymerase, a variety of transcription regulators involved in promotion and suppression of transcription bind to or act on such region to read the nucleotide sequence of the template gene and then synthesize (transcribe) complementary RNA.

A promoter used for polypeptide gene expression is not particularly limited, provided that such promoter can induce gene expression in a selected carbon source.

When a carbon source is methanol, examples of promoters for polypeptide gene expression include, but are not particularly limited to, the MOX promoter, the FMD promoter, the DHAS promoter, the AOX promoter, and the GAP promoter.

When a carbon source is glucose or glycerol, examples of promoters for polypeptide gene expression include, but are not particularly limited to, the GAP promoter, the TEF promoter, the LEU2 promoter, the URA3 promoter, the ADE promoter, the ADH1 promoter, and the PGK1 promoter.

4. Transformant

The transformant of the present invention can be obtained by transforming a host cell with the use of the vector described in 3. above.

The term "host cell" used in the present invention refers to a cell into which a vector is to be introduced. A host cell is not particularly limited, provided that a vector can be introduced thereinto.

Examples of host cells used for transformation include yeast cells, bacteria cells, fungal cells, insect cells, and animal cells, with yeast cells being preferable and methanol-assimilating yeasts being more preferable.

In general, "methanol-assimilating yeasts" can be cultured with the use of methanol as a sole carbon source. However, the ability to utilize methanol may be lost due to artificial modification or mutation.

Examples of methanol-assimilating yeasts include those belonging to the genera *Pichia*, *Ogataea*, *Candida*, *Torulopsis*, and *Komagataella*. A preferable example of yeasts of the genus *Pichia* is *Pichia methanolica*. Preferable examples of yeasts of the genus *Ogataea* include *Ogataea angusta*, *Ogataea polymorpha*, *Ogataea parapolymorpha*, and *Ogataea minuta*. A preferable example of yeasts of the genus *Candida* is *Candida boidinii*. Preferable examples of yeasts of the genus *Komagataella* include *Komagataella pastoris* and *Komagataella phaffii*.

Among the methanol-assimilating yeasts mentioned above, yeasts of the genus *Ogataea* or *Komagataella* are particularly preferable.

Preferable yeasts of the genus *Ogataea* are *Ogataea angusta*, *Ogataea polymorpha*, and *Ogataea parapolymorpha*. These three yeast species are closely related and they are also referred to as *Hansenula polymorpha* or *Pichia angusta*.

Specific examples of strains that can be used include *Ogataea angusta* NCYC495 (ATCC14754), *Ogataea polymorpha* 8V (ATCC34438), and *Ogataea parapolymorpha* DL-1 (ATCC26012). Such strains can be obtained from the American Type Culture Collection or other institutions. Strains derived from such strains can also be used in the present invention. Examples of leucine auxotrophs include NCYC495-derived BY4329, 8V-derived BY5242, and DL-1-derived BY5243. These strains can be distributed by the National BioResource Project.

Examples of preferable yeasts of the genus *Komagataella* include *Komagataella pastoris* and *Komagataella phaffii*.

Specific examples of strains that can be used include *Komagataella pastoris* Y-11430 and *Komagataella pastoris* X-33. Such strains can be obtained from the Northern Regional Research Laboratory or other institutions. In the present invention, strains derived from the strains mentioned above can also be used.

The term "transformant" used in the present invention refers to a host cell obtained by introducing the vector into a host cell. In the case of yeasts, for example, a vector may be introduced into a host cell via a known information, such as electroporation, the lithium acetate method, or the spheroplast method, although the techniques are not limited thereto. For example, *Ogataea angusta* is generally transformed via electroporation as described in "Highly-efficient electrotransformation of the yeast *Hansenula polymorpha*" (Curr. Genet., 25: 305.310.).

When a vector is transformed into a host cell, use of a selection marker gene, such as the auxotrophic marker gene or drug resistance gene, is preferable. A selection marker is not particularly limited. In the case of yeasts, the auxotrophic marker gene, such as the URA3 gene, the LEU2 gene, the ADE1 gene, or the HIS4 gene, can be selected by restoration of the prototrophic phenotype of the uracil-, leucine-, adenine-, or histidine-auxotrophs, respectively. The drug resistance gene, such as the G418 resistance gene, the zeocin resistance gene, or the hygromycin resistance gene, can be selected based on the resistance in a medium containing G418, zeocin, or hygromycin, respectively. The auxotrophic selection marker used when preparing a yeast host cannot be used unless the selection marker is destroyed. In such a case, the selection marker may be restored by methods known in the art.

When the vector is to be integrated into the host cell chromosome, it is preferable that DNA also comprise the homologous region of the host cell chromosome. The vector may be integrated into the chromosome via non-specific integration without using homologous regions, integration using a single homologous region, or double-integration using two homologous regions.

Regarding homologous regions, there may be 50% or higher sequence identity between the nucleotide sequence of the chromosome and that of the vector. While the length thereof is not particularly limited, it is preferably 50 bp or longer. Sequence identity between homologous regions is more preferably 70% or higher, further preferably 80% or higher, still further preferably 90% or higher, and most preferably 100%.

In the case of integration using a homologous region, for example, a homologous region of the plasmid vector is cleaved at one or more sites with restriction enzymes, so as to locate the homologous region at the end of a linear vector. Thus, transformation can be achieved. In the case of *Ogataea angusta*, for example, homologous integration into the MOX terminator can be carried out with the use of a linear expression vector obtained by cleaving the MOX terminator sequence at the NruI site or the EcoRV site.

The number of copies of expression cassettes per chromosome is not particularly limited. The location in the chromosome at which the vector has been integrated is not particularly limited, provided that the polypeptide is produced in the strain. When two or more copies of vectors are integrated into a transformant, a plurality of vectors may be integrated thereinto at the same position, or they may be integrated at different positions one by one.

5. Method of Protein Production

The method of protein production according to the present invention comprises the step of culturing the transformant described in 4. above and recovering a target protein from the culture product. The term "culture product" used herein refers to a cultured cell, a cultured strain, or a disrupted cell or strain, in addition to a culture supernatant.

According to the method for producing a target protein with the use of the transformant of the present invention, accordingly, the transformant is cultured and accumulated in the strain or a culture supernatant.

A transformant can be cultured in accordance with a method that is generally employed for culture of its host cells. When microorganisms such as yeasts are host cells, culture may be carried out in either a naturally-occurring or synthetic medium, provided that such medium contains carbon sources, nitrogen sources, inorganic salts, vitamins, and the like that can be utilized by microorganisms and such medium is capable of efficiently culturing a transformant. Examples of carbon sources that can be utilized by such microorganisms include sugars (e.g., glucose, sucrose, and maltose), organic acids (e.g., lactic acid, acetic acid, citric acid, and propionic acid), alcohols (e.g., methanol, ethanol, and glycerol), carbohydrates (e.g., paraffin), fats and oils (e.g., soybean oil and rapeseed oil), and mixtures of any thereof. Examples of nitrogen sources include ammonium sulfate, ammonium phosphate, urea, yeast extract, meat extract, peptone, and corn steep liquor. Examples of inorganic salts include monopotassium phosphate, dipotassium phosphate, magnesium phosphate, magnesium sulfate, sodium chloride, ferrous sulfate, manganese sulfate, copper sulfate, and calcium carbonate. Culture can be carried out in a batch or continuous system.

When methanol-assimilating yeasts are used as host cells according to a preferable embodiment of the present invention, the carbon source may be a single type of carbon source or two or more types of carbon sources selected from among glucose, glycerol, and methanol. Culture may be initiated in the presence of a carbon source, or a carbon source may be added during culture.

A transformant can be cultured under general conditions. In the case of yeasts, for example, culture can be carried out at a pH of 2.5 to 10.0 between 10° C. and 48° C. in an aerobic environment for 10 hours to 10 days.

The "target protein" of the present invention can be, for example, an enzyme derived from a microorganism or a protein produced by a multicellular organism, such as an animal or plant. Examples thereof include, but are not limited to, phytase, protein A, protein G, protein L, amylase, glucosidase, cellulase, lipase, protease, glutaminase, peptidase, nuclease, oxidase, lactase, xylanase, trypsin, pectinase, isomerase, and fluorescent protein. Human and/or animal therapeutic proteins are particularly preferable.

Specific examples of human and/or animal therapeutic proteins include hepatitis B virus surface antigen, hirudin, antibody, human antibody, partial antibody, human partial antibody, serum albumin, human serum albumin, epidermal growth factor, human epidermal growth factor, insulin, growth hormone, erythropoietin, interferon, antihemophilic factor, granulocyte colony-stimulating factor (G-CSF), granulocyte-macrophage colony-stimulating factor (GM-CSF), thrombopoietin, IL-1, IL-6, tissue plasminogen activator (TPA), urokinase, leptin, and stem cell growth factor (SCF).

The term "antibody" refers to a heterotetrameric protein composed of two L- and H-polypeptide chains joined by disulfide bonds. An antibody is not particularly limited, provided that it is capable of binding to a particular antigen.

The term "partial antibody" refers to Fab antibody, (Fab)2 antibody, scFv antibody, diabody antibody, or a derivative of any thereof. A partial antibody is not particularly limited, provided that it is capable of binding to a particular antigen. The term "Fab antibody" refers to a heteromeric protein composed of the L-chain and the Fd chain of the antibody joined by S—S bonds, or a heteromeric protein composed of the L-chain and the Fd chain of the antibody joined with each other without S—S bonds. A heteromeric protein is not particularly limited, provided that it is capable of binding to a particular antigen.

An amino acid constituting the target protein may be a naturally occurring, non-natural, or modified amino acid. The amino acid sequence of a protein may be artificially modified or de novo designed.

Target proteins produced with the use of the transformant of the present invention may be present in a culture supernatant, or proteins may be accumulated in the strain. Alternatively, proteins may be isolated therefrom via any technique. Proteins can be isolated from a culture supernatant or strain by performing known protein purification techniques in adequate combination. For example, the transformants are first cultured in an adequate medium, and a culture solution is subjected to centrifugation or filtration to remove strains from the culture supernatant. The obtained culture supernatant is then subjected to techniques such as salting-out (e.g., ammonium sulfate precipitation or sodium phosphate precipitation), solvent precipitation (e.g., protein fractional precipitation with acetone or ethanol), dialysis, gel filtration chromatography, ion-exchange chromatography, hydrophobic chromatography, affinity chromatography, reverse phase chromatography, or ultrafiltration. Any such techniques may be carried out alone or in combination, and the target proteins are isolated from the culture supernatant.

The isolated target proteins can be used without processing. Alternatively, such proteins may be subjected to pharmacological modification such as PEGylation, modification for the purpose of impartation of enzyme or isotope functions, or other types of modification before use. Also, proteins may be used in various forms of formulations.

When a target protein is to be secreted from the strain, a nucleotide sequence encoding a signal sequence may be introduced into the 5' end of the target protein gene. A nucleotide sequence encoding a signal sequence is not particularly limited, provided that such nucleotide sequence encodes a signal sequence that can be secreted and expressed by yeast. Examples thereof include nucleotide sequences encoding signal sequences of the mating factor α (MFα) of *Saccharomyces cerevisiae*, acid phosphatase (PHO1) of *Ogataea angusta*, acid phosphatase (PHO1) of *Komagataella pastoris*, invertase (SUC2) of *Saccharomyces cerevisiae*, PLB1 of *Saccharomyces cerevisiae*, bovine serum albumin (BSA), human serum albumin (HSA), and immunoglobulin.

In the present invention, a target protein promoter is not particularly limited, provided that it is capable of expressing a target protein in a transformant, and it is preferably a methanol-inducible promoter.

The methanol-inducible promoter of the present invention is not particularly limited, provided that it has transcription activity when a carbon source is methanol. For example, it is preferably the AOX1 promoter, the AOX2 promoter, the CAT promoter, the DHAS promoter, the FDH promoter, the FMD promoter, the GAP promoter, or the MOX promoter.

EXAMPLES

Hereafter, the present invention is described in greater detail with reference to the examples, although the present invention is not limited thereto. The recombinant DNA technology employed in the examples below is specifically described in the following books: Molecular Cloning 2nd Edition, Cold Spring Harbor Laboratory Press, 1989; and Current Protocols in Molecular Biology, Greene Publishing Associates and Wiley-Interscience.

In the examples below, plasmids used for yeast transformation were prepared by introducing the constructed antibody expression vectors and novel polypeptide expression vectors into *E. coli* DH5α competent cells (Takara Bio Inc.) and amplifying the resulting transformants via culture. Plasmids were prepared from plasmid-carrying strains using the QIAprep spin miniprep kit (QIAGEN).

The MOX promoter (SEQ ID NO: 1), the MOX terminator (SEQ ID NO: 2), and the LEU2 gene (SEQ ID NO: 3) used when constructing an antibody expression vector were prepared by PCR using, as a template, chromosome DNA of *Ogataea polymorpha* 8V. The mating factor α pre-pro signal gene (MFα, SEQ ID NO: 4) was prepared by PCR using chromosome DNA of *Saccharomyces cerevisiae* S288c as a template.

The antibody gene was prepared by PCR using, as templates, the L-chain gene (SEQ ID NO: 5) and the Fd-chain gene (SEQ ID NO: 6) (JP 2009-082033 A) chemically synthesized based on the disclosed sequence information of the fully humanized anti-TNF-α antibody (adalimumab; HUMIRA®).

In addition, the GAP promoter (SEQ ID NO: 7) used for construction of the novel polypeptide expression vector and the G418 resistance gene (SEQ ID NO: 8) controlled under the GAP promoter were obtained by PCR using, for example, chromosome DNA of *Ogataea angusta* NCYC495 or an adequate commercially available vector as templates.

The novel polypeptide (NP 1) gene (SEQ ID NO: 9) was prepared by subjecting a gene fragment comprising the SpeI recognition sequence and the BglII recognition sequence added to the 5' end and the 3' end of the polypeptide gene to PCR using chromosome DNA of *Ogataea angusta* NCYC495 as a template and primers 18 and 19 (SEQ ID NOs: 28 and 29), and then treating the resultant with SpeI and BglII and inserting into the XbaI/BamHI site of pUC19 so as to construct a plasmid comprising the polypeptide gene.

PCR was carried out using the Prime STAR HS DNA Polymerase (Takara Bio Inc.) in accordance with the manufacturer's instructions. Chromosome DNAs were prepared from yeasts using Dr. GenTLE® (Takara Bio Inc.) in accordance with the manufacturer's instructions.

Example 1

Construction of Fully Humanized Anti-TNF-α Fab Antibody Expression Vector

A gene fragment (SEQ ID NO: 10) having the HindIII-NotI-BamHI-SpeI-MunI-BglII-XbaI-EcoRI multicloning sites was fully synthesized, and the resultant was inserted into a site between HindIII and EcoRI of pUC19 to prepare pUC-1. Also, a gene fragment having the HindIII recognition sequences on both sides of the LEU2 gene was prepared by PCR using the primers 1 and 2 (SEQ ID NOs: 11 and 12), the fragment was treated with HindIII, and it was then inserted into the HindIII site of pUC-1 to prepare pUC-2. Subsequently, a gene fragment having the BamHI recognition sequences on both sides of the MOX promoter was prepared by PCR using the primers 3 and 4 (SEQ IDs NO: 13 and 14), the fragment was treated with BamHI, and it was then inserted into the BamHI site of pUC-2 to prepare pUC-Pmox.

A gene fragment having the MunI recognition sequences on both sides of the MOX promoter was prepared by PCR using the primers 5 and 6 (SEQ ID NOs: 15 and 16), the fragment was treated with MunI, and it was then inserted into the MunI site of pUC-Pmox to prepare pUC-PmoxPmox. Also, a gene fragment having the XbaI recognition sequences on both sides of the MOX terminator was prepared by PCR using the primers 7 and 8 (SEQ ID NOs: 17 and 18), the fragment was treated with XbaI, and it was then inserted into the XbaI site of pUC-PmoxPmox to prepare pUC-PmoxPmoxTm.

A gene fragment having the SpeI recognition sequence in a site upstream of MFα was prepared by PCR using the primers 9 and 10 (SEQ ID NOs: 19 and 20). A gene fragment having the 19-bp 3'-terminal fragment of MFα in a site upstream of the L-chain and the SpeI recognition sequence in a site downstream of the L-chain was prepared by PCR using the primers 11 and 12 (SEQ ID NOs: 21 and 22). These gene fragments were mixed to prepare a template, and PCR was carried out using the resulting template and the primers 9 and 12 to prepare a gene fragment having SpeI recognition sequences on both sides of a fusion gene of MFα and the L-chain. The resulting gene fragment was treated with SpeI and inserted into the SpeI sites of pUC-PmoxPmoxTm to prepare pUC-PmoxLPmoxTm.

Separately, a gene fragment having the BglII recognition sequence in a site upstream of MFα was prepared by PCR using the primers 13 (SEQ ID NO: 23) and 10. A gene fragment having the 19-bp 3'-terminal fragment of MFα in a site upstream of the Fd-chain and the BglII recognition sequence in a site downstream of the Fd-chain was prepared by PCR using the primers 14 and 15 (SEQ ID NOs: 24 and 25). These gene fragments were mixed to prepare a template, and PCR was carried out using the resulting template and the primers 13 and 15 to prepare a gene fragment having the BglII recognition sequences on both sides of a fusion gene of MFα and the Fd-chain. The resulting gene fragment was treated with BglII and inserted into the BglII site of pUC-PmoxLPmoxTm to prepare pUC-PmoxLPmoxFdTm. pUC-PmoxLPmoxFdTm is designed to allow expression of the L-chain and the Fd-chain of the Fab antibody under the control of the MOX promoter.

Example 2

Construction of Novel Polypeptide Expression Vector

A gene fragment having the XbaI recognition sequences on both sides of the MOX terminator was prepared by PCR using the primers 7 and 8, the fragment was treated with XbaI, and it was then inserted into the XbaI site of pUC-1 prepared in Example 1 to prepare pUCTm.

Subsequently, a gene fragment having the EcoRI recognition sequences on both sides of the G418 resistance gene controlled by the GAP promoter was prepared by PCR using the primers 16 and 17 (SEQ ID NOs: 26 and 27), the fragment was treated with EcoRI, and it was then inserted into the EcoRI site of pUCTm to prepare pUCTmG418. Subsequently, a gene fragment comprising the SpeI recognition sequence and the BglII recognition sequence added to the 5' end and the 3' end of the novel polypeptide gene, respectively, was subjected to PCR using a plasmid containing a novel polypeptide gene (NP 1) as a template and the primers 18 and 19 (SEQ ID NOs: 28 and 29). The resulting fragment was treated with SpeI and BglII and inserted into the SpeI/BglII site of pUCTmG418 to construct pUCNP1TmG418. Subsequently, a gene fragment having the BamHI recognition sequences on both sides of the GAP promoter was prepared by PCR using the primers 20 and 21 (SEQ ID NOs: 30 and 31), the fragment was treated with BamHI, and it was then inserted into the BamHI site of pUCNP1TmG418 to prepare pUCPgapNP1TmG418. This expression vector is designed to allow expression of the novel polypeptide (SEQ ID NO: 32) under the control of the GAP promoter.

Example 3

Preparation of Novel Polypeptide-expressing Yeast Host Cell

*E. coli* strains were transformed with the use of pUCPgapNP1TmG418 constructed in Example 2, the resulting transformants were cultured in 5 ml of 2YT medium (1.6% Bacto Tryptone (Difco), 1.0% Bacto Yeast Extract (Difco), and 0.5% NaCl), and pUCPgapNP1TmG418 was obtained from the resulting strains using the QIAprep spin miniprep kit (QIAGEN).

The plasmids were cleaved at the EcoRV or NruI site in the MOX terminator gene or the NodI site in the multicloning site to prepare linearized plasmids. With the use of such linearized pUCPgapNP1TmG418, *Ogataea angusta* and *Komagataella pastoris* were subjected to transformation in the manner described below.

The leucine-auxotrophs of *Ogataea angusta* NCYC495 were inoculated into 3 ml of YPD medium (1% Bacto Yeast Extract (Difco), 2% polypeptone (Nihon Pharmaceutical Co., Ltd.), and 2% glucose) and subjected to shake culture at 37° C. overnight to obtain a pre-culture solution. The obtained pre-culture solution (500 μl) was inoculated into 50 ml of YPD medium, shake culture was conducted at 37° C. until OD 600 reached 1 to 1.5, the culture product was centrifuged at 3,000×g and 20° C. for 10 minutes to harvest cells, and the cells were resuspended in 10 ml of 50 mM potassium phosphate buffer (pH 7.5) containing 250 μl of 1M DTT (final concentration: 25 mM). Similarly, the leucine-auxotrophs of *Komagataella pastoris* Y-11430 were inoculated into 3 ml of YPD medium (1% Bacto Yeast Extract (Difco), 2% polypeptone (Nihon Pharmaceutical Co., Ltd.), and 2% glucose) and subjected to shake culture at 30° C. overnight to obtain a pre-culture solution. The obtained pre-culture solution (500 μl) was inoculated into 50 ml of YPD medium, shake culture was conducted at 30° C. until OD 600 reached 1 to 1.5, the culture product was centrifuged at 3,000×g and 20° C. for 10 minutes to harvest cells, and the cells were resuspended in 10 ml of 50 mM potassium phosphate buffer (pH 7.5) containing 250 μl of 1M DTT (final concentration: 25 mM).

The suspension of *Ogataea angusta* and that of *Komagataella pastoris* were incubated at 37° C. and 30° C., respectively, for 15 minutes, the cells were harvested by centrifugation at 3,000×g and 20° C. for 10 minutes, and the resultants were washed with 50 ml of STM buffer (270 mM sucrose, 10 mM Tris-HCl, and 1 mM magnesium chloride; pH 7.5), which had been ice-cooled in advance. After the cells were harvested by centrifugation at 3,000×g and 4° C. for 10 minutes, the cells were washed again with 25 ml of ice-cooled STM buffer, and the cells were harvested by centrifugation at 3,000×g and 4° C. for 10 minutes. The cells were suspended in 250 μl of ice-cooled STM buffer at the end, and the resulting suspension was designated as a competent cell solution.

The competent cell solution (60 μl) was mixed with 3 μl each of the solutions of linearized pUCPgapNP1TmG418, and the mixtures were transferred into electroporation cuvettes (disposable cuvette; electrode gap: 2 mm; BM Equipment Co., Ltd.). The suspension of *Ogataea angusta* was pulsed at 7.5 kV/cm, 10 ρF, and 900Ω, the suspension of *Komagataella pastoris* was pulsed at 7.5 kV/cm, 25 μF, and 200Ω, the resultants were each suspended in 1 ml of YPD medium, and the suspension of *Ogataea angusta* and that of *Komagataella pastoris* were then allowed to stand at 37° C. and 30° C., respectively, for 1 hour. Thereafter, cells were harvested by centrifugation at 3,000×g at room temperature for 5 minutes, the harvested cells were suspended in 1 ml of YNBMSG medium (0.17% yeast nitrogen base w/o amino acid and ammonium sulfate (Difco) and 0.1% sodium glutamate), and the cells were harvested from the suspensions again by centrifugation at 3,000×g at room temperature for 5 minutes. The cells were resuspended in an adequate amount of YNBMSG medium, the resulting cell suspension was applied to the YNBMSGG418 selection agar plate (0.17% yeast nitrogen base w/o amino acid and ammonium sulfate (Difco), 0.1% sodium glutamate, 1.5% agarose, 2% glucose, 0.05% G418 disulfate, and 100 mg/l leucine), and the *Ogataea angusta* cells grown as a result of stationary culture at 37° C. for 3 days were selected. Thus, yeast host cells of *Ogataea angusta* expressing a novel polypeptide were obtained. Separately, the *Komagataella pastoris* cells grown as a result of stationary culture at 30° C. for 3 days were selected. Thus, yeast host cells of *Komagataella pastoris* expressing a novel polypeptide were obtained.

Example 4

Preparation of Transformants Expressing Novel Polypeptide and Fully Humanized Anti-TNF-α Fab Antibody

*E. coli* strains were transformed with the use of pUC-PmoxLPmoxFdTm constructed in Example 1, the resulting transformants were cultured in 5 ml of 2YT medium (1.6% Bacto Tryptone (Difco), 1.0% Bacto Yeast Extract (Difco), and 0.5% NaCl), and pUC-PmoxLPmoxFdTm was obtained from the resulting strains using the QIAprep spin miniprep kit (QIAGEN).

The plasmids were cleaved at the EcoRV site in the MOX terminator gene to prepare linearized plasmids. With the use of such linearized pUC-PmoxLPmoxFdTm, *Ogataea angusta* and *Komagataella pastoris* were subjected to transformation in the manner described below.

The yeast host cells of *Ogataea angusta* expressing a novel polypeptide obtained in Example 3 or the leucine-auxotrophs of *Ogataea angusta* NCYC495 were inoculated into 3 ml of YPD medium (1% Bacto Yeast Extract (Difco), 2% polypeptone (Nihon Pharmaceutical Co., Ltd.), and 2% glucose) and subjected to shake culture at 37° C. overnight to obtain a pre-culture solution. The obtained pre-culture solution (500 μl) was inoculated into 50 ml of YPD medium, shake culture was conducted at 37° C. until OD 600 reached 1 to 1.5, the culture product was centrifuged at 3,000×g and 20° C. for 10 minutes to harvest cells, and the cells were resuspended in 10 ml of 50 mM potassium phosphate buffer (pH 7.5) containing 250 μl of 1M DTT (final concentration: 25 mM). Similarly, the yeast host cells of *Komagataella pastoris* expressing a novel polypeptide obtained in Example 3 or the leucine-auxotrophs of *Komagataella pastoris* Y-11430 were inoculated into 3 ml of YPD medium (1% Bacto Yeast Extract (Difco), 2% polypeptone (Nihon Pharmaceutical Co., Ltd.), and 2% glucose) and subjected to shake culture at 30° C. overnight to obtain a pre-culture solution. The obtained pre-culture solution (500 μl) was inoculated into 50 ml of YPD medium, shake culture was conducted at 30° C. until OD 600 reached 1 to 1.5, the culture product was centrifuged at 3,000×g and 20° C. for 10 minutes to harvest cells, and the cells were resuspended in 10 ml of 50 mM potassium phosphate buffer (pH 7.5) containing 250 μl of 1M DTT (final concentration: 25 mM).

The suspension of *Ogataea angusta* and that of *Komagataella pastoris* were incubated at 37° C. and 30° C., respectively, for 15 minutes, the cells were harvested by centrifugation at 3,000×g and 20° C. for 10 minutes, and the resultants were washed with 50 ml of STM buffer (270 mM sucrose, 10 mM Tris-HCl, and 1 mM magnesium chloride; pH 7.5), which had been ice-cooled in advance. After the cells were harvested by centrifugation at 3,000×g and 4° C. for 10 minutes, the cells were washed again with 25 ml of ice-cooled STM buffer, and cells were then harvested by centrifugation at 3,000×g and 4° C. for 10 minutes. The cells were suspended in 250 μl of ice-cooled STM buffer at the end, and the resulting suspension was designated as a competent cell solution.

The competent cell solution (60 μl) was mixed with 3 μl each of the solutions of linearized pUC-PmoxLPmoxFdTm, and the mixtures were transferred into electroporation cuvettes (disposable cuvette; electrode gap: 2 mm; BM Equipment Co., Ltd.). The suspension of *Ogataea angusta* was pulsed at 7.5 kV/cm, 10 ρF, and 900Ω, the suspension of *Komagataella pastoris* was pulsed at 7.5 kV/cm, 25 μF, and 200Ω, the resultants were suspended in 1 ml of YPD medium, and the suspension of *Ogataea angusta* and that of *Komagataella pastoris* were then allowed to stand at 37° C. and 30° C., respectively, for 1 hour. Thereafter, cells were harvested by centrifugation at 3,000×g at room temperature for 5 minutes, the harvested cells were suspended in 1 ml of YNBMSG medium (0.17% yeast nitrogen base w/o amino acid and ammonium sulfate (Difco) and 0.1% sodium glutamate), and the cells were harvested from the suspension again by centrifugation at 3,000×g at room temperature for 5 minutes. The cells were resuspended in an adequate amount of YNBMSG medium, the transformants of the yeast host cells of *Ogataea angusta* expressing a novel polypeptide were applied to the YNBMSGG418 selection agar plate (0.17% yeast nitrogen base w/o amino acid and ammonium sulfate (Difco), 0.1% sodium glutamate, 1.5% agarose, 2% glucose, and 0.05% G418 disulfate), the transformants of the leucine-auxotrophs of *Ogataea angusta* NCYC495 were applied to the YNB selection agar plate (0.67% yeast nitrogen base w/o amino acid (Difco), 1.5% agarose, and 2% glucose), and the *Ogataea angusta* cells grown as a result of stationary culture at 37° C. for 3 days were selected. Thus, transformants of *Ogataea angusta* expressing a novel polypeptide and a fully humanized anti-TNF-α Fab antibody and transformants of *Ogataea angusta* expressing a fully humanized anti-TNF-α Fab antibody were obtained. The *Komagataella pastoris* cells grown as a result of stationary culture at 30° C. for 3 days were selected. Thus, transformants of *Komagataella pastoris* expressing a novel polypeptide and a fully humanized anti-TNF-α Fab antibody and transformants of *Komagataella pastoris* expressing a fully humanized anti-TNF-α Fab antibody were obtained.

Example 5

Culture of Transformants Expressing Novel Polypeptide and Fully Humanized Anti-TNF-α Fab Antibody The transformants expressing a novel polypeptide and a fully humanized anti-TNF-α Fab antibody and the transformants expressing a fully humanized anti-TNF-α Fab antibody obtained in Example 4 were inoculated into 2 ml of BMGY medium (1% Bacto Yeast Extract, 2% polypeptone (Nihon Pharmaceutical Co., Ltd.), 0.34% yeast nitrogen base w/o amino acid and ammonium sulfate (Difco), 1% ammonium sulfate, 0.4 mg/l biotin, 100 mM potassium phosphate (pH 6.0), and 2% glycerol) or BMGMY medium (1% Bacto Yeast Extract (Difco), 2% polypeptone (Nihon Pharmaceutical Co., Ltd.), 0.34% yeast nitrogen base w/o amino acid and ammonium sulfate (Difco), 1% ammonium sulfate, 0.4 mg/l biotin, 100 mM potassium phosphate (pH6.0), 1% glycerol, and 2% methanol) and subjected to shake culture at 30° C. and 120 rpm for 72 hours. The culture supernatant was then recovered by centrifugation at 12,000 rpm and 4° C. for 5 minutes. The cell density was assayed at OD 600.

Example 6

Measurement of Secretion Level of Fully Humanized Anti-TNF-α Fab Antibody by ELISA The secretion-expression level of the anti-TNF-α Fab antibody in the culture supernatant of the transformants expressing a novel polypeptide and a fully humanized anti-TNF-α Fab antibody was measured by sandwich ELISA (i.e., enzyme-linked immunosorbent assay) in the manner described below. The goat anti-human IgG (Fab-specific) antibody (SIGMA) diluted 2,500-fold with an immobilization buffer (a 0.1 N sodium bicarbonate solution; pH 9.6) was applied to an ELISA plate (MaxiSoap, Nunc) at 50 μl/well, and the plate was subjected to incubation at 4° C. overnight.

After the completion of incubation, the solution was removed from the wells, the wells were blocked with 250 μl of Immunoblock (Dainippon Sumitomo Pharma Co., Ltd.), and the plate was allowed to stand at room temperature for 1 hour. The product was washed three times with PBST buffer (8 g/l sodium chloride, 0.2 g/l potassium chloride, 1.15 g/l monosodium phosphate (anhydrous), 0.2 g/l potassium dihydrogen phosphate (anhydrous), and 0.1% Tween 20), serial dilutions of the standard Fab antibody (Anti-Human IgG Fab, Rockland) and the culture supernatants were added at 50 μl/well, and the reaction was allowed to proceed at room temperature for 1 hour.

After the plate was washed four times with PBST buffer, a secondary antibody solution diluted 8,000-fold with PBST buffer (secondary antibody: Anti-human IgG (Fab-specific)-HRP conjugate antibody (SIGMA)) was added at 50 μl/well, and the reaction was allowed to proceed at room temperature for 1 hour. After the plate was washed four times with PBST buffer, 50 μl of TMB-1 Component Microwell Peroxidase Substrate SureBlue (KPL) was added, and the reaction solution was allowed to stand at room temperature for 20 minutes. The reaction was terminated with the addition of 50 μl of TMB Stop Solution (KPL), and the absorbance at 450 nm was then measured using a microplate reader (Bench-Mark Plus, Bio-Rad). The Fab antibody in the culture supernatant was quantified using the calibration curve for the standard Fab antibody. The secretion-expression level of the anti-TNF-α Fab antibody determined by the above method and the cell density (OD 600) are shown in FIG. 1.

As a result, the secretion-expression level of the transformants expressing a novel polypeptide (pUCPgapNP1TmG418-introduced) and a fully humanized anti-TNF-α Fab antibody was found to be apparently higher than that of the transformants expressing a fully humanized anti-TNF-α Fab antibody into which no novel polypeptide genes had been introduced. Since the secretion-expression level was high in a methanol-containing medium (i.e., BMGMY medium), it is considered that activation of a methanol-inducible promoter of a target protein may be simultaneously achieved in combination with a morphological change in strains that enables efficient secretion and production of a target protein, which could not be achieved by conventional techniques, as a result of expression of the novel polypeptide according to the present invention.

INDUSTRIAL APPLICABILITY

The present invention is applicable in the field of the production of human and/or animal therapeutic proteins.

All publications, patents, and patent applications cited herein are incorporated herein by reference in their entirety.

The invention claimed is:

1. A method for producing a target protein comprising:
(i) culturing a transformant of a host cell, comprising:
a gene encoding the target protein operably linked to a methanol-inducible promoter, and
a vector which comprises a gene encoding a polypeptide, wherein the polypeptide gene comprises:
(a) a polynucleotide encoding a polypeptide comprising SEQ ID NO: 32,
(b) a polynucleotide encoding a polypeptide comprising an amino acid sequence with 95% or higher sequence identity with SEQ ID NO: 32, or
(c) a polynucleotide encoding a polypeptide comprising SEQ ID NO: 32 with up to 5 substitutions, deletions, insertions and/or additions of amino acids; and
(ii) expressing the polypeptide and expressing the target protein; and
(iii) recovering a target protein from the culture product.

2. The method of claim 1, wherein the culturing occurs in a culture medium which comprises methanol and/or glycerol, and optionally glucose.

3. The method of claim 1, wherein a polynucleotide encoding a signal sequence is at the 5' end of the target protein gene.

4. The method of claim 1, wherein a host cell is a yeast cell, bacteria cell, fungal cell, insect cell, or animal cell.

5. The method of claim 4, wherein the host cell is the yeast cell, and the yeast cell is a methanol-assimilating yeast cell.

6. The method of claim 5, wherein the methanol-assimilating yeast cell belongs to the genus *Ogataea* or *Komagataella*.

7. The method of claim 1, wherein the target protein is a human therapeutic protein.

8. The method of claim 1, wherein the polypeptide is not naturally expressed in the host cell.

9. The method of claim 1, wherein the methanol inducible promoter is also a glycerol inducible promoter.

10. The method of claim 1, wherein the polynucleotide is (a) a polynucleotide encoding a polypeptide comprising SEQ ID NO: 32.

11. The method of claim 1, wherein the polynucleotide is (b) a polynucleotide encoding a polypeptide comprising an amino acid sequence with 95% or higher sequence identity with SEQ ID NO: 32.

12. The method of claim 1, wherein the polynucleotide is (c) a polynucleotide encoding a polypeptide comprising SEQ ID NO: 32 with up to 5 substitutions, deletions, insertions and/or additions of amino acids.

* * * * *

SEQUENCE LISTING

<160> NUMBER OF SEQ ID NOS: 34

<210> SEQ ID NO 1
<211> LENGTH: 1511
<212> TYPE: DNA
<213> ORGANISM: Ogataea polymorpha

<400> SEQUENCE: 1

```
tcgacgcgga gaacgatctc ctcgagctgc tcgcggatca gcttgtggcc cggtaatgga      60
accaggccga cggcacgctc cttgcggacc acggtggctg gcgagcccag tttgtgaacg     120
aggtcgttta gaacgtcctg cgcaaagtcc agtgtcagat gaatgcctc ctcggaccaa     180
ttcagcatgt tctcgagcag ccatctgtct ttggagtaga agcgtaatct ctgctcctcg     240
ttactgtacc ggaagaggta gtttgcctcg ccgcccataa tgaacaggtt ctctttctgg     300
tggcctgtga gcagcgggga cgtctggacg gcgtcgatga ggcccttgag gcgctcgtag     360
tacttgttcg cgtcgctgta gccggccgcg gtgacgatac ccacatagag gtccttggcc     420
attagtttga tgaggtgggg caggatgggc gactcggcat cgaaattttt gccgtcgtcg     480
tacagtgtga tgtcaccatc gaatgtaatg agctgcagct gcgatctcg gatggttttg     540
gaatggaaga accgcgacat ctccaacagc tgggccgtgt tgagaatgag ccggacgtcg     600
ttgaacgagg gggccacaag ccggcgtttg ctgatgcgc ggcgctcgtc ctcgatgtag     660
aaggccttt ccagaggcag tctcgtgaag aagctgccaa cgctcggaac cagctgcacg     720
agccgagaca attcggggg ccggctttg gtcatttcaa tgttgtcgtc gatgaggagt     780
tcgaggtcgt ggaagatttc cgcgtagcgg cgttttgcct cagagtttac catgaggtcg     840
tccactgcag agatgccgtt gctcttcacc gcgtacagga cgaacggcgt ggccagcagg     900
cccttgatcc attctatgag gccatctcga cggtgttcct tgagtgcgta ctccactctg     960
tagcgactgg acatctcgag actgggcttg ctgtgctgga tgcaccaatt aattgttgcc    1020
gcatgcatcc ttgcaccgca agtttttaaa acccactcgc tttagccgtc gcgtaaaact    1080
tgtgaatctg gcaactgagg gggttctgca gccgcaaccg aacttttcgc ttcgaggacg    1140
cagctggatg gtgtcatgtg aggctctgtt tgctggcgta gcctacaacg tgaccttgcc    1200
taaccggacg gcgctaccca ctgctgtctg tgcctgctac cagaaaatca ccagagcagc    1260
agagggccga tgtggcaact ggtggggtgt cggacaggct gtttctccac agtgcaaatg    1320
cgggtgaacc ggccagaaag taaattctta tgctaccgtg cagcgactcc gacatcccca    1380
gttttgccc tacttgatca cagatggggt cagcgctgcc gctaagtgta cccaaccgtc    1440
cccacacggt ccatctataa atactgctgc cagtgcacgg tggtgacatc aatctaaagt    1500
acaaaaacaa a                                                         1511
```

<210> SEQ ID NO 2
<211> LENGTH: 607
<212> TYPE: DNA
<213> ORGANISM: Ogataea polymorpha

<400> SEQUENCE: 2

```
ggagacgtgg aaggacatac cgcttttgag aagcgtgttt gaaatagtt cttttctgg       60
tttatatcgt ttatgaagtg atgagatgaa aagctgaaat agcgagtata ggaaaattta    120
atgaaaatta aattaaatat tttcttaggc tattagtcac cttcaaaatg ccggccgctt    180
ctaagaacgt tgtcatgatc gacaactacg actcgtttac ctggaacctg tacgagtacc    240
tgtgtcagga gggagccaat gtcgaggttt tcaggaacga tcagatcacc attccggaga    300
```

```
ttgagcagct caagccggac gttgtggtga tatcccctgg tcctggccat ccaagaacag    360
actcgggaat atctcgcgac gtgatcagcc attttaaagg caagattcct gtctttggtg    420
tctgtatggg ccagcagtgt atcttcgagg agtttggcgg agacgtcgag tatgcgggcg    480
agattgtcca tggaaaaacg tccactgtta agcacgacaa cagggaatg ttcaaaaacg     540 ttccgcaaga tgttgctgtc accagatacc actcgctggc cggaacgctc aagtcgcttc    600
cggactg                                                              607
```

<210> SEQ ID NO 3
<211> LENGTH: 1251
<212> TYPE: DNA
<213> ORGANISM: Ogataea polymorpha

<400> SEQUENCE: 3

```
gagtccctga gtacgtaagc ggtttggtaa tacgaaataa aaagacagga atgagtaagt    60
ggatggtttt tcaattttc cggtaccggc gcaaaatagt tgcatcattt tgcaatcatg     120
agtaagaaca ttgtgcttct ccctggtgat cacgtgggcc ccgaggttgt tgcggaggcc    180
gtcaaggttc tcgaggctgt ctcgtcggca atcggcgtta agttcaactt ttccaagcac    240
ctgatcggcg gtgcctcgat cgatgcttat ggggtgccat tgtccgacga ggccctcgaa    300
gccgccaaga aggctgacgc cgttttgctt ggagccgtcg gaggacctaa gtggggaacc    360
ggctccgtgc gtcctgagca gggtctgttg aagatcagaa aagagctcaa cttgtacgcg    420
aacctgcgtc catgcagttt tgcttccgac gctcttctga agctatctcc actgaaatca    480
gaaatcgtca agggcactga ctttgttgtt gtgcgtgagt tggttggtgg aatctacttt    540
ggtgaccgca aggaggatgc cggcgacgga gttgccagcg acactgagag ctattctgtt    600
ccagaggtgc agagaatcac gagaatggcg gccttttgg cgctgcagag cgacccaccg     660
ctcccactgt ggtcgctgga caaagccaac gtgcttgcat cctcgcgttt gtggcggaag    720
actgttgagg agaccatcaa gaacgagttc ccgcagctga cggtgcagca ccagctgatc    780
gactcggcag ccatgatttt ggtcaagtcg ccaacgaaac tcaacggtgt cattgtcacc    840
aacaacatgt ttggcgacat catcagtgac gaggccagtg tgattcctgg gtctctgggc    900
ctgctgcctt ctgcctcgtt ggcgtctctg ccagacacaa acaaggcgtt tggtctttac    960
gagccctgcc acggctcggc gccagatttg gcccgcggca aggtcaatcc attggccaca    1020
attttgtctg ccgccatgat gctgaagctg tcgctggact tggtggatgc cggccgtgcg    1080
atcgagcagc ccgtcaagaa cgtcctggat gcaggtatca tgactgccga tttgggtgga    1140
agctcctcaa cacaggaagt tggtgatgct gttgcgcagg aggtggccaa gctactcaag    1200
aactaaataa gggagaaaaa aaagtaggat ctcgaataat tcctaaataa t             1251
```

<210> SEQ ID NO 4
<211> LENGTH: 255
<212> TYPE: DNA
<213> ORGANISM: Saccharomyces cerevisiae

<400> SEQUENCE: 4

```
atgagatttc cttcaatttt tactgcagtt ttattcgcag catcctccgc attagctgct    60
ccagtcaaca ctacaacaga agatgaaacg gcacaaattc cggctgaagc tgtcatcggt    120
tactcagatt tagaagggga tttcgatgtt gctgttttgc cattttccaa cagcacaaat    180
aacgggttat tgtttataaa tactactatt gccagcattg ctgctaaaga agaagggta    240
```
tctctcgaga aaaga                                              255

<210> SEQ ID NO 5
<211> LENGTH: 645
<212> TYPE: DNA
<213> ORGANISM: Artificial Sequence
<220> FEATURE:
<223> OTHER INFORMATION: Light chain gene

<400> SEQUENCE: 5
gacatccaga tgacccagtc tccatcctcc ctgtctgcat ctgtagggga cagagtcacc     60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa acgaactgtg gcggcgccat ctgtcttcat cttcccgcca    360
tctgatgagc agttgaaatc tggaactgcc tctgttgtgt gcctgctgaa taacttctat    420
cctcgagagg ccaaagtaca gtggaaggtg gataacgccc tccaatcggg taactcccag    480
gagagtgtca cagagcagga cagcaaggac agcacctaca gcctcagcag cacccctgacg   540 ctgagcaaag cagattacga gaaacacaaa gtctacgcct gcgaagtcac ccatcagggc    600
ctgagctcgc ccgtcacaaa gagcttcaac aggggagagt gttag                    645

<210> SEQ ID NO 6
<211> LENGTH: 675
<212> TYPE: DNA
<213> ORGANISM: Artificial Sequence
<220> FEATURE:
<223> OTHER INFORMATION: Fd chain gene

<400> SEQUENCE: 6
gaggtgcagc tggtggagtc tgggggaggc ttggtacagc ccggcaggtc cctgagactc     60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tgagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag ggaccctggt caccgtctcg    360
agtgctagct tcaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gttaa                                              675

<210> SEQ ID NO 7
<211> LENGTH: 284
<212> TYPE: DNA
<213> ORGANISM: Ogataea angusta

<400> SEQUENCE: 7
tacagagctt tatatcacct tactgaacgc tagagtagac ccaattcccg gctcacacca     60
cccttacatg cagagctaac caataaggta attaattaac actatatagc tcgtggtgaa    120

```
cactggcccg gagtagtcat acgtgtaggt ttttggcgtg atgaaaatca ggtggcgcac    180
gacttttcgt aaagttcggg agggagtgct gcaaacggca tataaggacc agttttctc    240 gcacattatc aattgctctt tagtacaaag ataatataga aaca                    284
```

<210> SEQ ID NO 8
<211> LENGTH: 1081
<212> TYPE: DNA
<213> ORGANISM: Artificial Sequence
<220> FEATURE:
<223> OTHER INFORMATION: GAP prompter and G418 resistance gene

<400> SEQUENCE: 8

```
tacagagctt tatatcacct tactgaacgc tagagtagac ccaattcccg gctcacacca    60
cccttacatg cagagctaac caataaggta attaattaac actatatagc tcgtggtgaa   120
cactggcccg gagtagtcat acgtgtaggt ttttggcgtg atgaaaatca ggtggcgcac   180
gacttttcgt aaagttcggg agggagtgct gcaaacggca tataaggacc agttttctc   240 gcacattatc aattgctctt tagtacaaag ataatataga aaccatatga ttgaacaaga   300
tggattgcac gcaggttctc cggccgcttg ggtggagagg ctattcggct atgactgggc   360
acaacagaca atcggctgct ctgatgccgc cgtgttccgg ctgtcagcgc aggggcgccc   420
ggttcttttt gtcaagaccg acctgtccgg tgccctgaat gaactgcagg acgaggcagc   480
gcggctatcg tggctggcca cgacgggcgt tccttgcgca gctgtgctcg acgttgtcac   540
tgaagcggga agggactggc tgctattggg cgaagtgccg gggcaggatc tcctgtcatc   600
tcaccttgct cctgccgaga agtatccat catggctgat gcaatgcggc ggctgcatac   660
gcttgatccg gctacctgcc cattcgacca ccaagcgaaa catcgcatcg agcgagcacg   720
tactcggatg aagccggtc ttgtcgatca ggatgatctg gacgaagagc atcagggct    780 cgcgccagcc gaactgttcg ccaggctcaa ggcgcgcatg cccgacggcg aggatctcgt   840
cgtgacccat ggcgatgcct gcttgccgaa tatcatggtg gaaaatggcc gcttttctgg   900
attcatcgac tgtggccggc tgggtgtggc ggaccgctat caggacatag cgttggctac   960
ccgtgatatt gctgaagagc ttggcggcga atgggctgac cgcttcctcg tgctttacgg  1020
tatcgccgct cccgattcgc agcgcatcgc cttctatcgc cttcttgacg agttcttctg  1080
a                                                                  1081
```

<210> SEQ ID NO 9
<211> LENGTH: 654
<212> TYPE: DNA
<213> ORGANISM: Ogataea angusta

<400> SEQUENCE: 9

```
atggatgaag ccagttcgca gtccgtcaac cagaggcatc atacaaaacc agcatcatta    60
gcatcaaatt cattattgct accgcccatc ttgtcctcat tcacgacacc ggtacaacca   120
ccctacaagc caagcttgac ctccactaat tatgcagtcc gggttccttc gttacccacg   180
ccccattcct tagacgccaa gatcataccg aatccaattg atctccgagg gacagcagag   240
agaaattcct cgcacgtagg cccaatcgct ccggctcgtg tcccgcgcag tctaccagac   300
gacggaaagg agaagatcag gaagccacag aaggtgtcca acgatccag aaagggctgt   360 ttaacgtgta ggttccgcaa gcgtaagtgc tgcgagacca gccggtttg caccgagtgc   420 aagcggttag gcataaagtg ctcctggatt acaaacggcc tcgaaaacaa aaacaagtcg   480
```
aagaagaatc ctgactttct tcgaaacgac gaatgctacg acgacatatt cggcgtcatc    540
aaagttgtcc gaggcaagat agactacaaa attgcagacg gctactttgt tgaaggcaac    600 aaaccccgg acgatgagct gtacaataca gaggcagaga cacacgaaac gtga           654

<210> SEQ ID NO 10
<211> LENGTH: 50
<212> TYPE: DNA
<213> ORGANISM: Artificial Sequence
<220> FEATURE:
<223> OTHER INFORMATION: Multi cloning site

<400> SEQUENCE: 10
aagcttgcgg ccgcggatcc actagtcaat tgagatcttc tagagaattc              50

<210> SEQ ID NO 11
<211> LENGTH: 35
<212> TYPE: DNA
<213> ORGANISM: Artificial Sequence
<220> FEATURE:
<223> OTHER INFORMATION: Primer 1

<400> SEQUENCE: 11
taaagcttga gtccctgagt acgtaagcgg tttgg                              35

<210> SEQ ID NO 12
<211> LENGTH: 33
<212> TYPE: DNA
<213> ORGANISM: Artificial Sequence
<220> FEATURE:
<223> OTHER INFORMATION: Primer 2

<400> SEQUENCE: 12
ataagcttat tatttaggaa ttattcgaga tcc                                33

<210> SEQ ID NO 13
<211> LENGTH: 30
<212> TYPE: DNA
<213> ORGANISM: Artificial Sequence
<220> FEATURE:
<223> OTHER INFORMATION: Primer 3

<400> SEQUENCE: 13
aatggatcct cgacgcggag aacgatctcc                                    30

<210> SEQ ID NO 14
<211> LENGTH: 31
<212> TYPE: DNA
<213> ORGANISM: Artificial Sequence
<220> FEATURE:
<223> OTHER INFORMATION: Primer 4

<400> SEQUENCE: 14
attggatcct tgtttttgt actttagatt g                                   31

<210> SEQ ID NO 15
<211> LENGTH: 30
<212> TYPE: DNA
<213> ORGANISM: Artificial Sequence
<220> FEATURE:
<223> OTHER INFORMATION: Primer 5

<400> SEQUENCE: 15
aatcaattgt cgacgcggag aacgatctcc                                    30

```
<210> SEQ ID NO 16
<211> LENGTH: 31
<212> TYPE: DNA
<213> ORGANISM: Artificial Sequence
<220> FEATURE:
<223> OTHER INFORMATION: Primer 6

<400> SEQUENCE: 16
attcaattgt tgtttttgt actttagatt g                              31

<210> SEQ ID NO 17
<211> LENGTH: 37
<212> TYPE: DNA
<213> ORGANISM: Artificial Sequence
<220> FEATURE:
<223> OTHER INFORMATION: Primer 7

<400> SEQUENCE: 17
taatctagag gagacgtgga aggacatacc gcttttg                       37

<210> SEQ ID NO 18
<211> LENGTH: 26
<212> TYPE: DNA
<213> ORGANISM: Artificial Sequence
<220> FEATURE:
<223> OTHER INFORMATION: Primer 8

<400> SEQUENCE: 18
gatcctctag acagtccgga agcgac                                   26

<210> SEQ ID NO 19
<211> LENGTH: 32
<212> TYPE: DNA
<213> ORGANISM: Artificial Sequence
<220> FEATURE:
<223> OTHER INFORMATION: Primer 9

<400> SEQUENCE: 19
tccactagta tgagatttcc ttcaattttt ac                            32

<210> SEQ ID NO 20
<211> LENGTH: 24
<212> TYPE: DNA
<213> ORGANISM: Artificial Sequence
<220> FEATURE:
<223> OTHER INFORMATION: Primer 10

<400> SEQUENCE: 20
tcttttctcg agagataccc cttc                                     24

<210> SEQ ID NO 21
<211> LENGTH: 39
<212> TYPE: DNA
<213> ORGANISM: Artificial Sequence
<220> FEATURE:
<223> OTHER INFORMATION: Primer 11

<400> SEQUENCE: 21
ggtatctctc gagaaaagag acatccagat gacccagtc                     39

<210> SEQ ID NO 22
<211> LENGTH: 32
<212> TYPE: DNA
<213> ORGANISM: Artificial Sequence
<220> FEATURE:
<223> OTHER INFORMATION: Primer 12
```

<400> SEQUENCE: 22
tccactagtt taacactctc ccctgttgaa gc        32

<210> SEQ ID NO 23
<211> LENGTH: 32
<212> TYPE: DNA
<213> ORGANISM: Artificial Sequence
<220> FEATURE:
<223> OTHER INFORMATION: Primer 13

<400> SEQUENCE: 23
tccagatcta tgagatttcc ttcaattttt ac        32

<210> SEQ ID NO 24
<211> LENGTH: 39
<212> TYPE: DNA
<213> ORGANISM: Artificial Sequence
<220> FEATURE:
<223> OTHER INFORMATION: Primer 14

<400> SEQUENCE: 24
ggtatctctc gagaaaagag aggtgcagct ggtggagtc        39

<210> SEQ ID NO 25
<211> LENGTH: 27
<212> TYPE: DNA
<213> ORGANISM: Artificial Sequence
<220> FEATURE:
<223> OTHER INFORMATION: Primer 15

<400> SEQUENCE: 25
ttgagatctt taacaagatt tgggctc        27

<210> SEQ ID NO 26
<211> LENGTH: 28
<212> TYPE: DNA
<213> ORGANISM: Artificial Sequence
<220> FEATURE:
<223> OTHER INFORMATION: Primer 16

<400> SEQUENCE: 26
ttagaattct acagagcttt atatcacc        28

<210> SEQ ID NO 27
<211> LENGTH: 29
<212> TYPE: DNA
<213> ORGANISM: Artificial Sequence
<220> FEATURE:
<223> OTHER INFORMATION: Primer 17

<400> SEQUENCE: 27
aatgaattcc ccgctcagaa gaactcgtc        29

<210> SEQ ID NO 28
<211> LENGTH: 30
<212> TYPE: DNA
<213> ORGANISM: Artificial Sequence
<220> FEATURE:
<223> OTHER INFORMATION: Primer 18

<400> SEQUENCE: 28
ttaactagta tggatgaagc cagttcgcag        30

<210> SEQ ID NO 29
<211> LENGTH: 33

```
<212> TYPE: DNA
<213> ORGANISM: Artificial Sequence
<220> FEATURE:
<223> OTHER INFORMATION: Primer 19

<400> SEQUENCE: 29
ttaagatctt cacgtttcgt gtgtctctgc ctc                              33

<210> SEQ ID NO 30
<211> LENGTH: 28
<212> TYPE: DNA
<213> ORGANISM: Artificial Sequence
<220> FEATURE:
<223> OTHER INFORMATION: Primer 20

<400> SEQUENCE: 30
ttaggatcct acagagcttt atatcacc                                   28

<210> SEQ ID NO 31
<211> LENGTH: 28
<212> TYPE: DNA
<213> ORGANISM: Artificial Sequence
<220> FEATURE:
<223> OTHER INFORMATION: Primer 21

<400> SEQUENCE: 31
aatggatcct gtttctatat tatctttg                                   28

<210> SEQ ID NO 32
<211> LENGTH: 217
<212> TYPE: PRT
<213> ORGANISM: Ogataea angusta

<400> SEQUENCE: 32
```

Met Asp Glu Ala Ser Ser Gln Ser Val Asn Gln Arg His His Thr Lys
1               5                   10                  15

Pro Ala Ser Leu Ala Ser Asn Ser Leu Leu Pro Pro Ile Leu Ser
            20                  25                  30

Ser Phe Thr Thr Pro Val Gln Pro Pro Tyr Lys Pro Ser Leu Thr Ser
        35                  40                  45

Thr Asn Tyr Ala Val Arg Val Pro Ser Leu Pro Thr Pro His Ser Leu
    50                  55                  60

Asp Ala Lys Ile Ile Pro Asn Pro Ile Asp Leu Arg Gly Thr Ala Glu
65                  70                  75                  80

Arg Asn Ser Ser His Val Gly Pro Ile Ala Pro Ala Arg Val Pro Arg
                85                  90                  95

Ser Leu Pro Asp Asp Gly Lys Glu Lys Ile Arg Lys Pro Gln Lys Val
            100                 105                 110

Ser Lys Arg Ser Arg Lys Gly Cys Leu Thr Cys Arg Phe Arg Lys Arg
        115                 120                 125

Lys Cys Cys Glu Thr Lys Pro Val Cys Thr Glu Cys Lys Arg Leu Gly
    130                 135                 140

Ile Lys Cys Ser Trp Ile Thr Asn Gly Leu Glu Asn Lys Asn Lys Ser
145                 150                 155                 160

Lys Lys Asn Pro Asp Phe Leu Arg Asn Asp Glu Cys Tyr Asp Asp Ile
                165                 170                 175

Phe Gly Val Ile Lys Val Val Arg Gly Lys Ile Asp Tyr Lys Ile Ala
            180                 185                 190

Asp Gly Tyr Phe Val Glu Gly Asn Lys Pro Pro Asp Asp Glu Leu Tyr
        195                 200                 205

```
Asn Thr Glu Ala Glu Thr His Glu Thr
    210                 215

<210> SEQ ID NO 33
<211> LENGTH: 36
<212> TYPE: PRT
<213> ORGANISM: Ogataea angusta

<400> SEQUENCE: 33

Lys Arg Ser Arg Lys Gly Cys Leu Thr Cys Arg Phe Arg Lys Arg Lys
1               5                   10                  15

Cys Cys Glu Thr Lys Pro Val Cys Thr Glu Cys Lys Arg Leu Gly Ile
            20                  25                  30

Lys Cys Ser Trp
        35

<210> SEQ ID NO 34
<211> LENGTH: 108
<212> TYPE: DNA
<213> ORGANISM: Ogataea angusta

<400> SEQUENCE: 34
aaacgatcca gaaagggctg tttaacgtgt aggttccgca agcgtaagtg ctgcgagacc      60
aagccggttt gcaccgagtg caagcggtta ggcataaagt gctcctgg                  108
```